US005380653A

United States Patent [19]

Palva

[11] Patent Number: 5,380,653

[45] Date of Patent: Jan. 10, 1995

[54] EXPRESSION VECTORS AND METHODS FOR INTRACELLULAR PROTEIN PRODUCTION IN BASCILLUS

[75] Inventor: Ilkka Palva, Helsinki, Finland

[73] Assignee: The Finnish National Public Health Institute, Finland

[21] Appl. No.: 947,888

[22] Filed: Sep. 18, 1992

Related U.S. Application Data

[63] Continuation of Ser. No. 308,861, Feb. 10, 1989, abandoned, which is a continuation-in-part of Ser. No. 129,357, Nov. 30, 1987, Pat. No. 5,010,015, which is a continuation of Ser. No. 939,244, Dec. 5, 1986, abandoned, which is a continuation of Ser. No. 336,405, Dec. 31, 1981, abandoned.

[30] Foreign Application Priority Data

Dec. 31, 1980 [FI] Finland ................................ 804081

[51] Int. Cl.$^6$ ...................... C12N 15/09; C12N 15/54; C12N 15/62; C12N 15/75

[52] U.S. Cl. .................................. 435/69.7; 435/69.1; 435/69.3; 435/69.8; 435/172.3; 435/193; 435/320.1; 435/252.31; 536/23.4; 536/23.7; 935/47; 935/48

[58] Field of Search .................... 435/69.1, 69.7, 69.8, 435/183, 172.3, 320.1, 252.31; 536/23.4, 24.1, 23.7; 935/29, 47, 48, 39, 44

[56] References Cited

FOREIGN PATENT DOCUMENTS 0232229 8/1987 European Pat. Off. .
0281530 7/1988 European Pat. Off. .
2091268 12/1981 United Kingdom .
2133408 7/1984 United Kingdom .

OTHER PUBLICATIONS

Kallio "Expression and Regulation of the *Bacillus Amyliquefaciens* alpha-Amylase Gene in *Bacillus subtilis*," Thesis Dissertation (1987), pp. 1-27.
Palva, I., et al., Gene 15:43-51 (1981).
Palva, I., Gene 19:81-87 (1982).
Palva, I., et al., *Proc. Natl. Acad. Sci. USA* 79:5582-5586 (1982).
Petterson, R. F., et al, Gene 24:15-27 (1983).
Kallio, P., et al., *Journal of General Microbiology* 132:677-687 (1986).
Takkinen, K., et al., *Journal of Biological Chemistry* 258:1007-1013 (1983).
Emr, S. D., et al., *Nature* 285:82-85 (1980).
Fahnestock, S. R., et al., *Journal of Bacteriology* 165:796-804 (1986).
Sibakov, *Eur. J. Biochem.* 155:577-581 (1986).
Ulmanen et al., J. Bacteriol. 162(1):176-182 (1985).

*Primary Examiner*—Richard A. Schwartz
*Assistant Examiner*—J. LeGuyader
*Attorney, Agent, or Firm*—Virginia H. Meyer

[57] ABSTRACT

The invention relates to recombinant DNA molecules and to methods for producing proteins by means of said molecules. Particularly, the present invention relates to recombinant DNA molecules which are capable of being synthesized in Bacillus strain bacteria comprising the regulation and deleted non-functional signal sequence of the a-amylase gene of *B. amyloliquefaciens*, or a substantial part thereof, to which sequence a structural gene of any desired homologous or heterologous protein or peptide may be joined. These recombinant DNA molecules can be used, for example, to achieve intracellular expression of any desired protein or peptide in Bacillus strain bacteria.

12 Claims, 5 Drawing Sheets

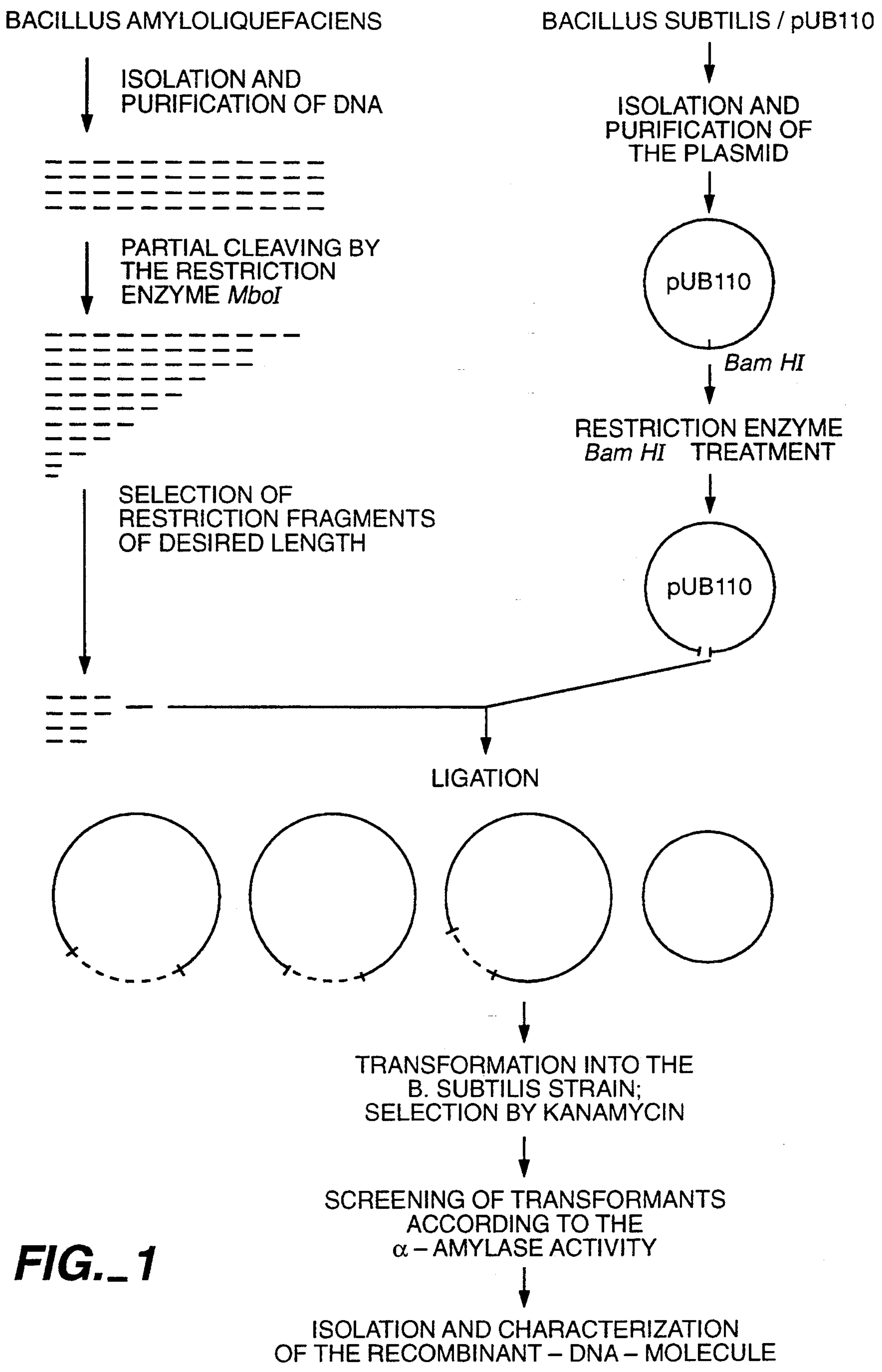
*FIG._1*

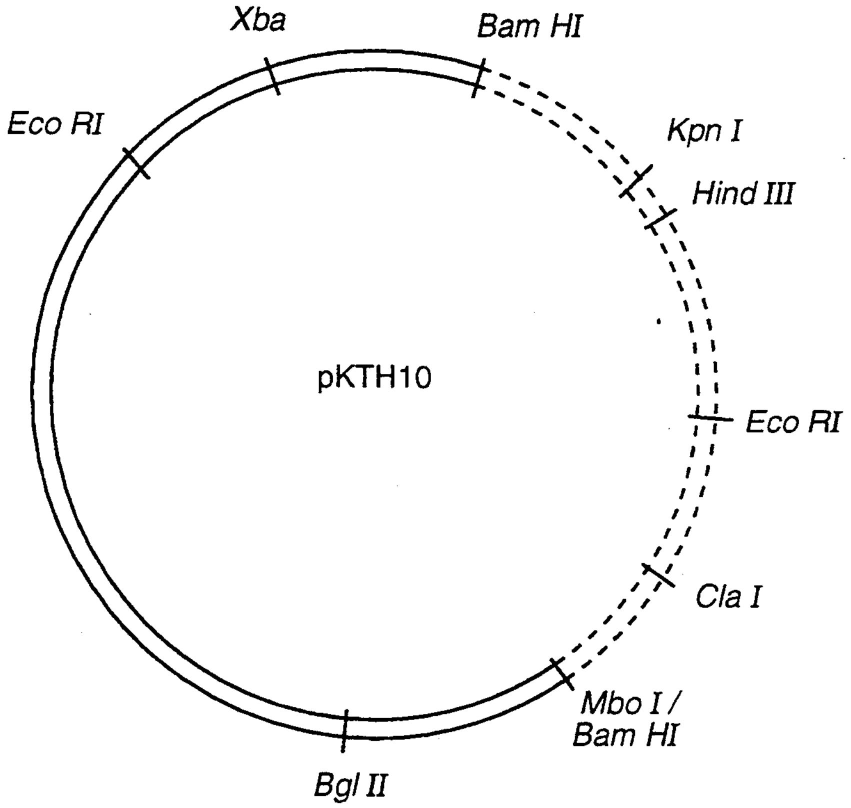
FIG._2

Translation of DNA sequence BAAAM.

DE BACILLUS AMYLOLIQUEFACIENS ALPHA–AMYLASE GENE

OS BACILLUS AMYLOLIQUEFACIENS; MARBURG STRAIN–IH

Total number of bases: 2010.
Translation from base 1 to base 480.
Done on (absolute) phase(s): 2.
Using the Universal genetic code.

```
         10        20        30        40        50        60
          |         |         |         |         |         |
CGATTGTTTGAGAAAAGAAGAAGACCATAAAAATACCTTGTCTGTCATCAGACAGGGTAT
ClaI

         70        80        90       100       110       120
          |         |         |         |         |         |
TTTTTATGCTGTCCAGACTGTCCGCTGTGTAAAAATAAGGAATAAAGGGGGGTTGTTATT

        130       140       150       160       170       180
          |         |         |         |         |         |
ATTTTACTGATATGTAAAATATAATTTGTATAAGAAAATGAGAGGGAGAGGAAACATGAT
                                                         M  I

        190       200       210       220       230       240
          |         |         |         |         |         |
TCAAAAACGAAAGCGGACAGTTTCGTTCAGACTTGTGCTTATGTGCACGCTGTTATTTGT
 Q  K  R  K  R  T  V  S  F  R  L  V  L  M  C  T  L  L  F  V

        250       260       270       280       290       300
          |         |         |         |         |         |
CAGTTTGCCGATTACAAAAACATCAGCCGTAAATGGCACGCTGATGCAGTATTTTGAATG
 S  L  P  I  T  K  T  S  A  V  N  G  T  L  M  Q  Y  F  E  W

        310       320       330       340       350       360
          |         |         |         |         |         |
GTATACGCCGAACGACGGCCAGCATTGGAAACGATTGCAGAATGATGCGGAACATTTATC
 Y  T  P  N  D  G  Q  H  W  K  R  L  Q  N  D  A  E  H  L  S

        370       380       390       400       410       420
          |         |         |         |         |         |
GGATATCGGAATCACTGCCGTCTGGATTCCTCCCGCATACAAAGGATTGAGCCAATCCGA
 D  I  G  I  T  A  V  W  I  P  P  A  Y  K  G  L  S  Q  S  D

        430       440       450       460       470       480
          |         |         |         |         |         |
TAACGGATACGGACCTTATGATTTGTATGATTTAGGAGAATTCCAGCAAAAAGGGACGGT
 N  G  Y  G  P  Y  D  L  Y  D  L  G  E  F  Q  Q  K  G  T  V
                                       EcoRI
```

FIG._3

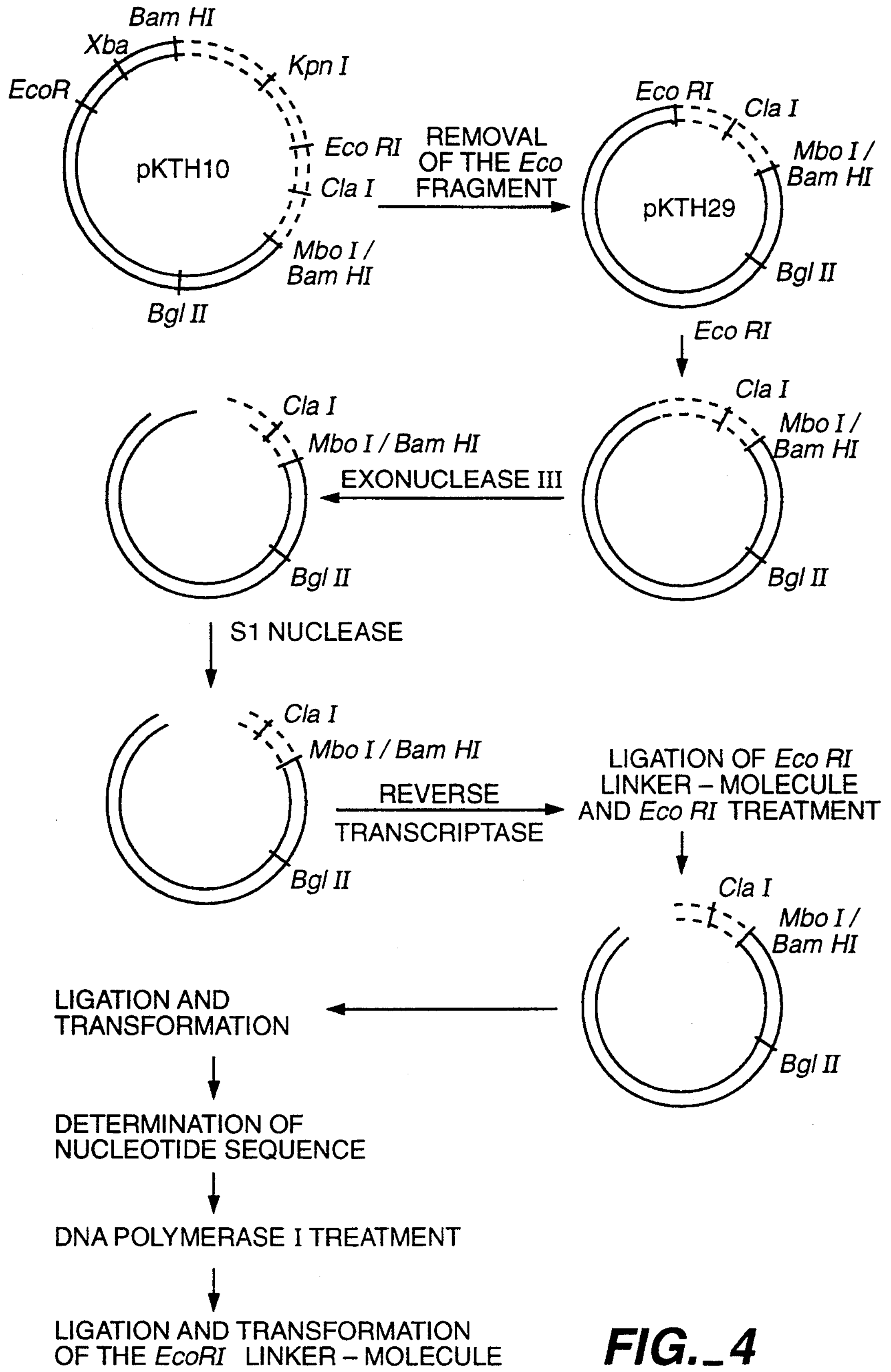
FIG._4

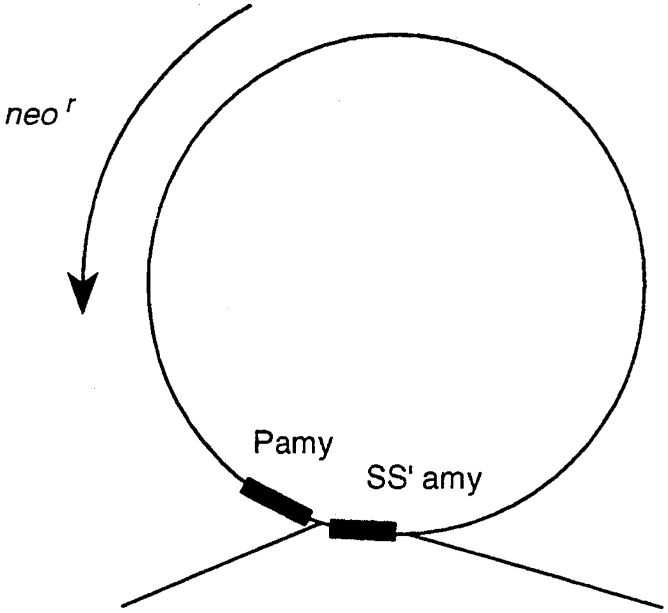
pKTH39
Met Ile Gln Lys Arg Lys Arg Asn Ser
ATG ATT CAA AAA CGA AAG CGG AAT TCC
EcoRI
pKTH1781
Met Ile Gln Lys Arg Lys Arg Asn Ser Glu Ala
ATG ATT CAA AAA CGA AAG CGG AAT TCG GAA GCT T
HindIII
pKTH1784
Met Ile Gln Lys Arg Lys Arg Asn Leu Ser
ATG ATT CAA AAA CGA AAG CGG AAT TTA AGC TT
HindIII
FIG._5

EXPRESSION VECTORS AND METHODS FOR INTRACELLULAR PROTEIN PRODUCTION IN BASCILLUS

This is a continuation of application Ser. No. 07/308,861, filed Feb. 10, 1989, now abandoned, which is a continuation-in-part of application Ser. No. 07/129,357, filed Nov. 30, 1987, now U.S. Pat. No. 5,010,015, which is a continuation of application Ser. No. 06/939,244, filed Dec. 5, 1986, now abandoned, which is a continuation of application Ser. No. 06/336,405, filed Dec. 31, 1981, now abandoned.

BACKGROUND OF THE INVENTION

This invention is concerned with recombinant DNA molecules, and methods for producing proteins by said molecules. The invention is further concerned with recombinant DNA molecules that are synthesized in Bacillus strain bacteria and are known to have DNA which codes for exoenzymes excreted by them and that are present in tens of copies of Bacillus strain bacteria; as well as with recombinant DNA molecules modified from the above recombinant DNA molecules that are known to have DNA which contains the regulation and excretion signals of the α-amylase gene of *B. amyloliquefaciens,* to which signals a gene of any protein can be joined. The invention is particularly related to the regulation and deleted, non-functional excretion signal of the α-amylase gene of *B. amyloliquefaciens,* to which a desired structural protein may be joined. It has been found that, for certain structural proteins, Bacillus expression may be surprisingly enhanced, and is to be desired, when intracellular production is achieved according to this aspect of the invention. As will be described in the following, these recombinant DNA molecules can be used, for example, to intensify the α-amylase production in Bacillus strain bacteria, and their modifications to produce any desired homologous or heterologous protein or peptide in Bacillus strain bacteria.

Recent development in molecular biology has created new possibilities for protein production in bacteria by recombinant DNA techniques. In addition to the possibility of producing proteins of eukaryotic cells in bacteria by recombinant DNA techniques, the synthesis of the proteins of the bacteria themselves can be significantly improved by increasing the number of the copies of the desired gene in the cell. The number of the gene copies in a bacterium cell can be increased by joining the gene to such a plasmid or virus DNA molecule as is found in the cell in several, usually 10 to 100, copies. The increased number of the gene copies in a cell usually also leads to a corresponding increase in the protein synthesis expressed by the gene.

Even though several experiments of this type have been carried out using *E. coli* and plasmid or virus DNA molecules replicating in it as host bacterium, the use of Bacillus strain bacteria as hosts is only beginning (Gryczan et al., *Molecular General Genet.* 117:459–467 (1979); Keggins et al., *Proc. Natl. Acad. Sci. USA* 75:1423–1427 (1978); Yoneda et al., *Biochem. Biophys. Res. Commun.* 91:1556–1564 (1979)).

SUMMARY OF THE INVENTION

As the preceding discussion demonstrates, none of the methods publicized so far are concerned with increasing the production of the exoenzyme of a Bacillus strain bacterium in Bacillus strain bacteria in a manner which would allow the gene coding for the exoenzyme to be replicated by joining it to the plasmid that is present in the Bacillus strain bacterium in several copies (Part I of the invention), nor are any of the publicized methods concerned with producing proteins by a method in which the regulation and secretion signals of the gene of the enzyme secreted by the Bacillus strain bacteria have been joined to the gene of the protein desired to be produced (Part II of the invention). As an example of the first part of the invention, by which the production of Bacillus strain bacterium exoenzymes can be intensified through increasing the number of the genes of the desired exoenzyme in the cell, the transfer of the Bacillus α-amylase gene is presented.

Accordingly, it is an object of the present invention to provide recombinant DNA molecules comprising the regulation and deleted non-functional signal sequence of the α-amylase gene of *B. amyloliquefaciens,* or a substantial part thereof. It is a further object of the invention to provide such molecules, wherein said deleted non-functional signal sequence comprises a nucleotide sequence selected from the group consisting of pKTH 39, pKTH 1781 and pKTH 1784 as shown in FIG. 5, or a substantial part thereof.

In yet another aspect, the present invention provides for a recombinant DNA molecule comprising a deleted non-functional sequence comprising any of the following sequences:

ATG ATT CAA AAA CGA AAG CGG AAT TCC;

ATG ATT CAA AAA CGA AAG CGG AAT TCG GAA GCT T;

ATG ATT CAA AAA CGA AAG CGG AAT TTA AGC TT;

or substantial parts thereof.

An additional object of the invention is to provide vectors comprising the recombinant DNA molecules described above. Such vectors may further comprise, in accordance with the present invention, a nucleotide sequence encoding a desired homologous or heterologous protein or peptide, or a substantial part thereof. It is an additional object of the invention to provide such vectors in which the said nucleotide sequence encodes a desired protein selected from the group consisting of chloramphenicol acetyl transferase and pertussis toxin or its subunits.

In another aspect, the present invention provides for a Bacillus host comprising the vectors described above Yet another object of the present invention is to provide a method for obtaining intracellular expression of a desired homologous or heterologous protein or peptide, or a substantial part thereof, in a Bacillus host, comprising (a) ligating a desired homologous or heterologous protein or peptide, or a substantial part thereof, to a vector comprising a recombinant DNA molecule as mentioned above;

(b) transfecting a desired Bacillus host with the product of step (a); and (c) culturing the Bacillus host of step (b) under conditions allowing intracellular expression of said desired homologous or heterologous protein or peptide.

In another embodiment, the present invention provides for a homologous or heterologous protein or peptide, or a substantial part thereof, produced according to the method of the invention.

These and other objects and aspects of the present invention will be evident to those of skill from the following description and claims.

BRIEF DESCRIPTION OF THE DRAWINGS

FIG. 1 is a flow sheet illustrating the procedure of one embodiment of the invention in which the recombinant DNA molecule is prepared, isolated and characterized;

FIG. 2 is a schematic illustration of the plasmid pKTH 10 and the general structure of the obtained recombinant DNA molecule;

FIG. 3 is a representation of the nucleotide sequence (shown in the 5'-3' direction) of bases 1–480 of the α-amylase gene, showing the ClaI and EcoRI restriction sites, and in which the cleavage site of the signal sequence is indicated by an arrow;

FIG. 4 is a flow sheet illustrating the preparation of the recombinant DNA molecule of the present invention containing the regulation and excretion signals of the Bacillus strain α-amylase gene; and FIG. 5 shows the nucleotide sequence of Bacillus expression vectors pKTH 39, pKTH 1781 and pKTH 1784, having an α-amylase promoter (Palva et al., (1981)) and a truncated α-amylase signal sequence.

DETAILED DESCRIPTION OF THE INVENTION

FIG. 1 shows the performance of the first part of this invention. The genome of the whole bacterium is isolated from the Bacillus strain bacterium producing α-amylase, and cleaved by a restriction enzyme. DNA sequences of a desired length are joined to the plasmid molecule cleaved by the restriction enzyme. According to this invention, the genome of the bacterium can be cleaved by the restriction enzyme MboI, and pUB110 can be used as the plasmid which can be cleaved by the restriction enzyme BamHI. It must be noticed that a corresponding recombinant DNA molecule can be prepared also by using other restriction enzymes or plasmids, and an experienced scientist can choose between various restriction enzyme/plasmid combinations, and still remain within the scope of this invention.

After joining the DNA sequences with the plasmid molecules, the obtained recombinant DNA molecules are transferred into the host bacterium, and from the population of host bacteria those bacterium cells are screened that have received a gene coding for α-amylase, joined to the plasmid. The screening is based on the achieved ability of the transformed cells to produce α-amylase.

*Bacillus subtilis* strain is used as the host bacterium in this invention. When the above-mentioned recombinant DNA molecule has been transferred into the strain, the gene coding for α-amylase is present in it in about 50 copies. This increases the α-amylase production of the strain to about 500-fold, as compared to normal *B. subtilis* strains. The 500-fold increase of the α-amylase production is due, on the one hand, to the regulation signal of the α-amylase gene of the *B. amyloliquefaciens* strain used as the initial strain being about ten times more effective than that of the *B. subtilis* α-amylase gene, and, on the other hand, to the number of α-amylase genes growing 50-fold. In laboratory conditions, a *B. subtilis* strain containing a recombinant DNA molecule produces 3–5 times more α-amylase than the *B. amyloliquefaciens* strain used in the isolation of the gene.

The recombinant DNA molecule is isolated from the *B. subtilis* strain, and characterized by restriction enzymes and definition of the base order. FIG. 2 shows the pKTH 10 of the obtained recombinant DNA molecule, the exclusive restriction enzyme cleavage sites in the α-amylase gene or its regulation signal, and the general structure of the recombinant DNA molecule. FIG. 3 shows part of the α-amylase gene base order starting at the cleavage site of the restriction enzyme EcoRI.

The recombinant DNA molecule concerned in this invention consists of the regulation and excretion signals of the Bacillus strain α-amylase gene, and of plasmid molecules that are present in the Bacillus strain bacteria in several copies in such a manner as allows the gene of any protein to be joined at the end of the excretion signal of the α-amylase gene, which results in the desired protein being produced in the Bacillus strain bacterium. In another embodiment, the signal sequence of the α-amylase gene is deleted (omitted) from the recombinant DNA molecule introduced into the Bacillus host. Accordingly, production of the desired protein will be intracellular. Recovery can be accomplished by well known methods. The preparation of this recombinant DNA molecule is shown in FIG. 4. A shortened α-amylase-based expression vector is shown in FIG. 5. Thus, by "regulation and deleted nonfunctional signal sequence" of the α-amylase gene of *B. amyloliquefaciens* is meant the regulation sequence and at least the initiation methionine of the signal sequence or a larger N-terminal part of the signal sequence.

By "substantial part thereof" is meant a recombinant DNA molecule which, while it does not include the entire regulation and deleted non-functional signal sequence of the α-amylase gene of *B. amyloliquefaciens,* does include a sufficient part of the specified sequence to achieve the same or substantially the same function in controlling intracellular expression of a desired structural gene in a Bacillus host.

Similarly, "substantial part thereof" used herein in reference to a homologous or heterologous protein or peptide or to the gene encoding such protein or peptide is meant to include the "fragments," "variants," "analogs," or "chemical derivatives" of a molecule. A "fragment" of a molecule, such as any of the cDNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences,* 16th ed., Mack Publishing Co., Easton, Pa. (1980). A "functional derivative" of a gene according to the present invention is meant to include "fragments," "variants," or "analogues" of the gene, which may be "substantially similar" in nucleotide sequence, and which encode a molecule possessing similar activity.

Generally, in preparing the recombinant DNA molecules of the present invention, most of the α-amylase structural gene is first removed by EcoRI restriction enzyme treatment from the recombinant DNA molecule containing the α-amylase gene. The obtained DNA molecule is cleaved by the restriction enzyme and shortened by exonuclease III and S1 nuclease to remove the remaining α-amylase structure gene, whereafter it is secured by a reverse transcriptase enzyme, such that the ends of the molecule are double-stranded. A DNA linker molecule containing the EcoRI cleavage site is then joined to the cleaved and shortened molecule. The location of the DNA linker in the recombinant DNA molecule is determined by defining the DNA base order at the joining site. The last nucleotides in the α-amylase structure gene are removed by DNA polymerase I treatment, and the new DNA linker is joined at the end of the secretion signal of the α-amylase gene. Alternatively, the α-amylase secretion signal may also be substantially removed.

In either case, at the resulting restriction enzyme cleavage site of the DNA linker molecule it is possible to join the structural gene of any other homologous or heterologous protein or peptide, or a substantial part thereof. For example, the β-lactamase of *E. coli,* the DNA sequence or part of it any α, β or γ interferon, chloramphenicol acetyl transferase and Pertussis toxin or any of its subunits are suitable proteins and peptides. The protein or peptide coded by the joined gene will then be produced and excreted, or produced intracellularly, in the Bacillus strain bacterium by the aid of the regulation and excretion signals, or regulation region alone, respectively, of the α-amylase gene. Intracellularly produced protein or peptide may be recovered from the Bacillus host by well known methods.

The choice of particular homologous or heterologous proteins or peptides for intracellular production in accordance with the present invention will be made by those of skill without undue experimentation, with regard to well known principles and established empirical methods. In Bacillus hosts, cytoplasmic proteins, proteins which are very hydrophobic, and proteins which exhibit strong protein-protein interactions are poor candidates for secretion. Such proteins generally will be good candidates for intracellular production by means of the invention.

Thus, proteins which are not normally secreted in their homologous host cells will be good candidates for intracellular production in Bacillus employing the regulation and deleted non-functional secretion signal sequence of the present invention. While the present inventor does not wish to be bound by any particular theory, two hypotheses have been forwarded to explain the molecular mechanisms underlying protein secretion and the behavior of cytoplasmic proteins.

First, it has been suggested that, in addition to the signal sequence, there is in the mature part of a secreted protein some form of positive or active information that is also essential to the secretion process. Cytoplasmic proteins would lack this necessary active information.

An alternate hypothesis is that all information necessary to accomplish secretion resides within the signal sequence, but some passive information exists within the mature part of the protein which acts to inhibit secretion in some heterologous host systems.

Recent data appear to support the latter hypothesis, and two types of passive information have been suggested. One possibility is that this passive information is contained directly within the primary protein sequence. For example, this could take the form of a long, highly hydrophobic region, or of a group of several positively charged amino acid residues. Such types of structures would function as a transfer-stop signal during secretion. While transfer-stop signals typically are found in proteins which are transported into cell membranes, they are unlikely to be found in cytoplasmic proteins.

A second possibility is that the critical information resides in the kinetics of protein folding. In other words, the rate at which a protein assumes its tertiary structure during and after translation determines whether or not it will be secreted. Proteins which fold slowly probably are capable of being secreted irrespective of whether they are cytoplasmic, membrane-resident, or are normally excreted in their homologous hosts cells.

The kinetics of protein folding can depend upon the protein sequence. It is known, for example, that certain types of sequences fold more quickly than others. Further, preferred codon usage in a given host may also affect folding. Also, the N-terminal region of a secretory protein can interact with components of the secretion machinery during translation. Such components could include proteins found on the inner surface of the cytoplasmic membrane, the membrane itself, or possibly cytoplasmic components. It is not likely that the particular N-terminal amino acid sequence plays a role, since no homology has been reported among the N-terminal regions of different secretory proteins. It thus is possible that the secretion machinery recognizes a protein to be secreted through an interaction with the protein's polypeptide backbone. Such an interaction would block the formation of a stable tertiary protein structure, and would render the protein compatible with the secretion machinery.

DETAILED DESCRIPTION OF THE PERFORMANCE OF THE FIRST PART OF THE INVENTION

Isolation, Purification and Cleavage of the Genome from Bacillus Strain Bacteria

*B. amyloliquefaciens* strain was used as the bacterium strain. The strain was grown overnight in a rich nutrient solution, the cells were harvested and washed in a 0.0015M sodium citrate—0.015M NaCl buffer. The washed cells were suspended ($2\times10^{11}$ cells, i.e., a culture of 200 ml) into 2 ml of 20% w/v saccharose—50 mM Tris HCl solution (pH 8.0). 20 mg lysozyme, 20 mg pronase and 2 ml 1% w/v Sarkosyl®—0.1M EDTA solution (pH 8.0) were added, and the solution was incubated for 15 hours at 37° C. 6.5 ml $H_2O$ and such an amount of solid CsCl as to make the refraction index of the lysate 1.4100, were added, and the lysate was centrifuged (Beckman Ti 50 rotor, 36,000 rpm, 48 hours, 10° C.). The centrifuged lysate was divided into fractions, and those fractions that were presumed to contain the bacterial genome on the basis of their viscosity, were collected and dialyzed for 30 hours against a 10 mM Tris HCl—1 mM EDTA—0.1M NaCl buffer (pH 8.0) at 4° C.

The obtained genome preparate was extracted three times with phenol, and the phenol was removed by ether extraction. The DNA was purified by centrifugation in linear 15–30% w/v saccharose—0.1M NaCl—50 mM Tris HCl—1 mM EDTA, 0.1% sodium lauryl sulphate (pH 8.0) gradient; Beckman SW27 rotor, 22,000 rpm, for 16 hours at 22° C., whereafter the gradient was fractioned, and those fractions were collected whose DNA sequences were $\geq 15 \times 10^6$ dalton, and the DNA was precipitated by ethanol.

The genome preparate of *B. amyloliquefaciens* thus isolated was incompletely cleaved by the restriction enzyme MboI, and the cleaved DNA sequences were sorted out according to their size in the above saccharose gradient (Beckman SW27 rotor, 22,000 rpm, 16 hours at 22° C.). Those fractions whose DNA sequences were $1.5-5 \times 10^6$ dalton were harvested and the DNA was precipitated by ethanol.

Isolation and Cleavage of the Transfer Vector by Restriction Enzyme

The plasmid pUB110 was used as a transfer vector. The plasmid was isolated and purified from the *Bacillus subtilis* strain SB202 as described earlier (Gryczan et al., *J. Bacteriol.* 134:318–329 (1978)). The purified plasmid preparate was cleaved with the restriction enzyme BamHI, which has only one cleavage site in the plasmid molecule. The linearity of the plasmid molecule was controlled by gel electrophoresis.

Combination of the *B. amyloliquefaciens* Genome Strands to the Transfer Vector

The *B. amyloliquefaciens* genome strands that had been cleaved by the enzyme MboI and selected on the basis of their size, were mixed with the pUB110 plasmid cleaved by the enzyme BamHI in 10 mM Tris HCl—1 mM EDTA buffer (pH 8.0) in a DNA-concentration ratio of 1:3, with the total volume of 120 μl and with the total DNA concentration of 180 μg/ml. The solution was heated for 5 minutes at 65° C., the 13 μl 66 mM Tris HCl—6.6 mM MgCl$_2$—100 mM dithiothreitol—10 mM ATP buffer (pH 7.8) and 5 μl T$_4$-DNA ligase (20 Weiss units) were added to the chilled solution. The ligase solution was incubated for 3 hours at 23° C., and the ligation result was controlled by gel electrophoresis.

Transfer of the Recombinant DNA Molecule into the Host Bacterium

A *B. subtilis* 1A197 strain with the genotype sacA321, metB5, arol1907, amy$^-$, was used as the host bacterium. The strain was obtained from Bacillus Genetic Stock Center (Ohio State University, U.S.A.), and its phenotype Amy$^-$ was mapped by bacteriogenetic methods as mutations in the structure gene of the enzyme coding for α-amylase. The strain was made competent, i.e., capable of receiving DNA in a manner described previously (Anagnostopoulos et al., *J. Bacteriol.* 81:741–746 (1961)). The recombinant DNA molecules prepared by ligation as described above, were mixed with the competent host bacteria, and the mixture was kept for 30 min at 37° C. The mixture was then spread on bacterium plates with kanamycin antibiotics to prevent the growth of all those bacteria that had not received a plasmid. The plates were kept for 30 hours at 37° C., during which time the host bacteria with a plasmid or a *B. amyloliquefaciens* genome strand joined to it, grew into small colonies.

Detection of Host Bacteria in which the *B. amyloliquefaciens* Gene Coding for α-amylase is Joined to Plasmid pUB110

The bacterial colonies described above were replicated on new nutrient plates that were grown for 30 hours at 37° C. The obtained bacterial cultures were treated with I-KI solution using a method described earlier (*J. Bacteriol.* 119:416–424 (1974)), which resulted in a white ring forming around those bacterial colonies that had received a recombinant DNA molecule containing a gene coding for α-amylase. The corresponding colonies were collected from the original bacterium plates and the bacteria were subjected to several successive purification growths.

Isolation and Characterization of the Recombinant DNA Molecule

The recombinant DNA molecule was isolated and purified from the host bacterium by a method described earlier (Gryczan et al., *J. Bacteriol.* 134:318–329 (1978)). The molecule was characterized by various restriction enzymes, and the location of the gene coding for α-amylase was preliminarily determined by following the inactivation of the gene when joining extra DNA sequences at various sites of the recombinant DNA molecule. The base order of the gene coding for α-amylase was then determined by a method described earlier (Maxam, A. et al., *Proc. Natl. Acad. Sci. USA* 74:560–564 (1977)).

Determination of the α-amylase Activity

The modified host bacterium *B. subtilis* IHO 6064 (sacA321, metB5), which has a gene coding for α-amylase in plasmid pUB110, was grown in a liquid nutrient medium (Luria broth) by aerating at 37° C. Samples were taken from the culture liquid at 2-hour intervals, from which the α-amylase activity was determined by Phadebas ® tablets.

DETAILED DESCRIPTION OF THE PERFORMANCE OF THE SECOND PART OF THE INVENTION

Removal of EcoRI Fragment from Plasmid pKTH 10

The plasmid pKTH 10 was cleaved at the cleavage site EcoRI (FIG. 2). The obtained DNA sequences (about 1 μg) were ligated together again in 66 mM Tris HCl—6.6 mM MgCl$_2$—100 mM dithiothreitol—10 mM ATP buffer (pH 7.8), and 0.5 μl T$_4$-DNA ligase (2 Weiss units) was added. The ligation solution was incubated for 3 hours at 23° C., whereafter the competent *B. subtilis* IHO 6064 strain was transformed by it in a manner described above. The cells were spread on bacterium plates containing kanamycin and grown overnight at 37° C. An α-amylase-negative colony was screened from the obtained transformants by the I-KI method using starch plates, and a plasmid was isolated from the colony in a manner described earlier (Gryczan et al., *J. Bacteriol.* 134:318–329 (1978)). The missing EcoRI-KpnI-HindIII-EcoRI fragment in the obtained plasmid preparate pKTH 29 was controlled by gel electrophoresis.

Shortening of Plasmid pKTH 29 by Exonuclease Treatment

The plasmid pKTH 29 (100 μl, 500 μg/ml) was cleaved by the restriction enzyme EcoRI. After this treatment, 0.5 μl 1M dithiothreitol and 10 μl exonuclease III (0.25 units, Biolabs) were added to the solution. The solution was incubated for 1–3 minutes at 37° C., and the reaction was stopped in a 70° C. waterbath. The DNA was precipitated from the solution by ethanol and dissolved in a 0.3M NaCl—0.03M sodium acetate—3 mM $ZnCl_2$ buffer (pH 4.5). Ten μl S1-nuclease (25 units/ml, Boehringer Mannheim) was added and the solution was incubated for 30 minutes at 37° C. and for 10 min at 4° C. After the incubations, the preparate was extracted with phenol, the phenol was removed by ether extraction, and the DNA was precipitated by ethanol. The dried DNA was dissolved into 40 μl 10 mM Tris HCl—1 mM EDTA buffer (pH 8.0), and 10 μl 150 mM Tris—180 mM KCl—40 mM $MgCl_2$—3.0 mM dithiothreitol buffer (pH 8.3), 5 μl dNTP mixture, in which to each nucleotide-tri-phosphate 10 mM of the solution was mixed in equimolar ratio, and 2 μl reverse transcriptase enzyme (Beard, 13 units/μl) were added. The solution was incubated for 30 minutes at 37° C. and the reaction was stopped by incubation at 65° C. for 7 minutes. The DNA was purified by preparative agarose electrophoresis (LTG, Low Gelling Temperature), and the plasmid zones that had been dyed with ethidium bromide were cut off from the gel. The DNA was extracted from the agarose by phenol at 65° C., the phenol extraction was repeated at 20° C., and the phenol was removed by ether extraction. The DNA was precipitated by ethanol, and the precipitate was washed with 70% ethanol and dried.

Phosphorylation of EcoRI Linker Molecule and Its Combination to the Plasmid

Five μl $^{32}P$ γ-ATP (10 mCi/ml, 3000 Ci/mol), 1.7 μl 600 mM Tris HCl—66 mM $MgCl_2$—100 mM dithiothreitol buffer (pH 8.0) and 0.5 μl $T_4$-polynucleotide kinase were added to 10 μl EcoRI linker molecule solution (EcoRI linker, Collaborative Research, 50 μg/ml). The solution was incubated for 30 minutes at 37° C., whereafter 5 μl 10 mM ATP was added, and the incubation was continued for 30 min at 37° C. The dried pKTH 29 preparate that had been treated with exonuclease, was dissolved into 5 μl of the solution containing phosphorylated EcoRI-linker-molecule described above. 0.5 μl 10 mM ATP, 0.5 μl 1 mM spermidine and 0.5 μl $T_4$-DNA-ligase (2 Weiss units) were added to the solution. The solution was incubated for 3 hours at 23° C., whereafter it was diluted to 20 μl in 40 mM Tris HCl—100 mM NaCl—10 mM $MgCl_2$-buffer (pH 7.6). Fifteen units of EcoRI enzyme (Biolabs) were added, and the solution was incubated for 12 hours at 37° C. The reaction was stopped by incubation at 65° C. for 10 minutes. The preparate treated with EcoRI was gel filtered through a 1 ml Sepharose 4B column. Two mM Tris—HCl—0.1 mM EDTA (pH 7.5) was used as elution buffer in the filtering. The filtrate was harvested in 35 μl fractions, and the fractions containing plasmid were identified by their radioactivity, collected and dried. The dried DNA was dissolved into 20 μl 66 mM Tris HCl—6.6 mM $MgCl_2$—10 mM dithiothreitol buffer (pH 8.0), and 1.5 μl 10 mM ATP and 0.3 μl $T_4$-DNA-ligase were added. The solution was incubated for 3 hours at 23° C., whereafter the competent *B. subtilis* IHO 6064 strain was transformed by the plasmid preparate, and the cells were cultivated on bacterium plates containing kanamycin.

The plasmids were isolated from the transformants by a method described earlier (Gryczan et al., *J. Bacteriol.* 134:318–329 (1978)), and the plasmids were first characterized by gel electrophoresis, whereafter their DNA base sequence at both ends of the EcoRI linker molecule was determined. In this way, plasmids pKTH 38 and pKTH 39 were obtained from the plasmid pKTH 29.

In the plasmid pKTH 38, the EcoRI linker molecule is located 90 nucleotide pairs after the cleavage site of the excretion signal in the area of the α-amylase structural gene. In the plasmid pKTH 39, the EcoRI linker molecule is located 16 nucleotide pairs after the initiation methionine of the α-amylase gene in the area of the signal sequence.

In order to join the linker molecule at the joining site of the excretion signal or in the immediate vicinity thereof, the plasmid pKTH 38 was cleaved with EcoRI. Three portions of 10 μg of the cleaved plasmid were each suspended in 115 μl 20 mM Tris, 600 mM NaCl, 12 mM $MgCl_2$, 12 mM $CuCl_2$, 1 mM EDTA buffer (pH 8.1). Ten μl BAL-31 enzyme (Bethesda Research Laboratories, BRL, 40 U/ml) were added to each plasmid portion, and the tubes were incubated for 5, 6 and 7 minutes in a water bath of 30° C. The reaction was stopped by adding 0.5M EDTA, pH 8.0, so as to obtain a final concentration of 12 mM. The DNA portions treated with BAL-31 were combined, extracted twice with phenol and precipitated with ethanol. The ethanol precipitate was suspended in 75 μl 63 mM Tris, 6.3 mM $MgCl_2$ buffer (pH 8.0), and to the solution were added 5 μl 1 mM dATP, 1 mM dGTP, 1 mM dCTP, and 1 mM dTTP, and finally 5 μl T4 polymerase (PL-Biochemicals, 5 U/μl). The solution was incubated for 80 minutes at 11° C. The reaction was stopped by adding 0.5 EDTA as above, and the solution was extracted with phenol and the DNA was precipitated with ethanol. The ethanol precipitate was dissolved in 250 μl 10 mM Tris, 1 mM EDTA buffer (pH 8.0). To 55 μl of this solution were added 50 μl phosphorylated Hind III linker molecule (BRL, 75 pmol), 5 μl 660 mM Tris, 100 mM $MgCl_2$, 50 mM dithiothreitol buffer (pH 7.5), and 10 μl T4 DNA ligase (BRL, 2 U/μl). The mixture was incubated for 15 hours at 15° C. and for 10 minutes at 65° C. The DNA was precipitated by adding isopropanol, the DNA precipitate was washed with 70% ethanol and, after drying in vacuo, suspended in 100 μl 10 mM Tris, 50 mM NaCl, 5 mM MgCl, 5 mM dithiothreitol buffer (pH 8.0). Three μl of Hind III restriction enzyme (BRL, 10 U//μl) were added to the suspension, and the solution was incubated for 4 hours at 37° C. and for 10 minutes at 65° C. The DNA was purified by electrophoresis in 0.8% LGT agarose gel (Marine Colloids Inc.), at 30 V, for 15 hours. The linear plasmid zone was cut off from the gel, and the DNA was extracted at 65° C. with phenol and was precipitated with ethanol. The ethanol precipitate was dissolved in 35 μl 66 mM Tris, 10 mM MgCl, 5 mM dithiothreitol buffer (pH 7.5) to which was added 1.5 μl 10 mM rATP and 1.5 μl T4 DNA ligase (BRL, 2 U/μl). The mixture was incubated for 3 hours at 22° C. and transformed into the competent *B. subtilis* IHO 6135 strain, and the cells were cultivated on nutrient medium plates containing kanamycin. The plasmids were isolated from the transformants according to a method described earlier, and the location of the Hind III linker molecule in the plasmids was determined by means of DNA sequencing. In this way a series of plasmids was obtained in which the Hind III linker molecule is located immediately after the excretion signal or in different positions after the cleavage site of the excretion signal in the area of the α-amylase structure gene.

With respect to the plasmid pKTH 39, in order to join the linker molecule at the joining site of the signal sequence or in the immediate vicinity thereof, an analogous approach to that described above for the plasmid pKTH 38 is employed. In using the plasmid pKTH 39, which contains the deleted signal sequence of the α-amylase gene of *B. amyloliquefaciens,* the desired structural gene can thus be inserted either at the EcoRI site, or at the same location using an in vitro modified site as described, for example, in Example 3, or at any location intermediate between the initiation codon (-met) and the EcoRI site, by well known methods. The creation of a new joint site at the desired location may be accomplished by methods known to those of skill, including but not limited to site directed in vitro mutagenesis, polymerase chain reaction (PCR), or by synthesizing in vitro the required promoter fragment, all of which may be accomplished with the exercise of routine skill with an appreciation of the teaching of the present invention.

In addition to the plasmid pKTH 39, the above-described expression unit of the α-amylase gene can be incorporated into any number of suitable Bacillus replicative vectors. Alternatively, it may be integrated into the chromosome of host Bacillus in multiple copies. According to either chosen method, the expression unit of the present invention is suitable for the intracellular expression of a wide variety of structural genes in Bacillus hosts. The choice of whether to employ an α-amylase expression unit with or without the shortened or deleted signal sequence will be made by those of skill, depending upon the nature of the desired structural gene, in order to obtain optimal expression and recovery of gene product. It has been found, for example, that intracellular expression of Pertussis toxin according to the present invention is advantageous, and accordingly, a shortened α-amylase expression unit is preferred for this purpose.

TABLE

| | −31 Met | Phe | Gln | | −3 Thr | Ser | −1 Ala | +1 Val | Asn | Gly | Thr | Leu | Met | Gln | Tyr | Phe | Glu | Trp | Tyr | Thr | Pro | Asn |
|---|---|---|---|---|---|---|---|---|---|---|---|---|---|---|---|---|---|---|---|---|---|---|
| pKTH 10 | ATG | ATT | CAA | ... | ACA | TCA | GCC | GTA | AAT | GGC | ACG | CTG | ATG | CAG | TAT | TTT | GAA | TGG | TAT | ACG | CCG | AAC |
| pKTH 50 | ATG | ATT | CAA | ... | ACA | TCA | GCC | GCAAGCTTGC | | | | | | | | | | | | | | |
| pKTH 51 | ATG | ATT | CAA | ... | ACA | TCA | GCC | GCAAGCTTGC | | | | | | | | | | | | | | |
| pKTH 52 | ATG | ATT | CAA | ... | ACA | TCA | GCC | G | GCAAGCTTGC | | | | | | | | | | | | | |
| pKTH 53 | ATG | ATT | CAA | ... | ACA | TCA | GCC | GTA | AAT | GGC | AC | GCAAGCTTGC | | | | | | | | | | |
| pKTH 54 | ATG | ATT | CAA | ... | ACA | TCA | GCC | GTA | AAT | GGC | ACG | GCAAGCTTGC | | | | | | | | | | |
| pKTH 55 | ATG | ATT | CAA | ... | ACA | TCA | GCC | GTA | AAT | GGC | ACG | C | GCAAGCTTGC | | | | | | | | | |
| pKTH 56 | ATG | ATT | CAA | ... | ACA | TCA | GCC | GTA | AAT | GGC | ACG | CT | GCAAGCTTGC | | | | | | | | | |
| pKTH 57 | ATG | ATT | CAA | ... | ACA | TCA | GCC | GTA | AAT | GGC | ACG | CTG | ATG | CAG | TAT | TTT | G | GCAAGCTTGC | | | | |
| pKTH 58 | ATG | ATT | CAA | ... | ACA | TCA | GCC | GTA | AAT | GGC | ACG | CTG | ATG | CAG | TAT | TTT | GAA | TGG | GCAAGCTTGC | | | |
| pKTH 59 | ATG | ATT | CAA | ... | ACA | TCA | GCC | GTA | AAT | GGC | ACG | CTG | ATG | CAG | TAT | TTT | GAA | TGG | TAT | ACG | CCG | GCA ... |

The DNA sequence coding for the amino acids of any desired protein can be joined to the cleavage sites formed by these Hind III linker molecules whereby, as appears from the above examples, a bacterium of the Bacillus strain will produce and excrete said protein on its substrate.

A wide variety of proteins may be produced as illustrated by the following listing, presented by general categories:

A. Antigenic proteins of microbes and protozoa: Capsule, outer membrane and Fimbria proteins from the following sources: *Bacteroides fragilis, Fusobacterium spp., Bordetella pertussis, Haemophilus influenzae, Yersinia enterocolitica, Yersinia pestis, Branhamella catarrhalis, Escherichia coli, Klebsiella pneumonia, Vibrio cholerae, Proteus mirabilis, Pseudomonas aeruginosa, Serratia marcescens, Legionella pneumophila, Neisseria gonorrhoeae, Neisseria meningitidis, Salmonella typhimurium, Salmonella typhi, Salmonella paratyphi B, Mycobacterium tyberculosis, Chlamydia trachomatis,* and *Shigella spp.*

Protein toxins produced by the following bacteria: *Staphylococcus aureus, Pseudomonas aeruginosa, Clostridium spp., Escherichia coli, Yersinia pestis, Vibrio cholerae, Bordetella pertussis,* M-protein of the *Streptococcus pyogenes* bacterium, excreted enzymes of *Streptococcus mutans.*

Surface proteins of the following organisms (in all phases of development): *Plasmodium spp., Toxoplasma spp., Leishmania Schistosoma spp., Trypanosoma spp.*

Membrane proteins of the following microorganisms: *Mycoplasma pneumoniae, Mycoplasma hominis,* contagious protein of *Streptococcus spp.,* and contagious protein of *Staphylococcus aureus.*

B. Antigen proteins of viruses: HA and NA proteins of myxoviruses (influenza A H1–H12, influenza B, influenza C); HN and F proteins of paramyxoviruses (parainfluenze 1–4, Newcastle disease virus, Measles virus, Respiratory syncytial virus, Parotitis virus, Distemper virus); G protein of Rabies virus; E1 and E2 proteins of alfaviruses (Chikungunya, Western, Eastern, Venezuelan equine encephalitis virus, O'nyong-nyong virus, Semliki Forest virus, Sindbis virus); V1 and V3 proteins of flavin viruses (Denque 1–4, Japanese encephalitis virus, Mite encephalitis viruses, Murray Valley encephalitis virus, Kyasanur Forest disease virus, Looping ill virus, Omsk hemorrhagic fever virus); surface proteins of German measles virus; surface proteins of Hog Cholera virus; surface proteins of Equine arthritis virus; G1 and G2 proteins of Bunya viruses (Rift Valley fever virus, Crimean hemorrhagic fever virus, California encephalitis virus, Phlebotomus fever virus); G1 and G2 proteins of arena viruses (Lassa fever virus, Lymphatic chorion meningitis virus); proteins V1–V4 of picorna viruses (polio 1–3, Coxsackie A viruses 1–24, Coxsackie B viruses 1–6, ECHO viruses 1–8, 11–34, Hepatitis A virus, Human rhino viruses 1–113); surface proteins of rota viruses; surface proteins of herpes viruses (HSV 1, 2, Cytomegalo virus, Epstein-Barr virus, Equine abortion virus); VP1–VP3 proteins of papova viruses (BK virus, Human wart virus); proteins of parvo viruses (mink enteritis virus, Bovine parvo virus, Feline parvo virus, Procine parvo virus); structure proteins of Human hepatitis B virus; surface proteins of Ebola and Marburg viruses; and Hexone, pentone and fiber proteins of adeno viruses, (Human adeno viruses 1–33).

C. Industrial enzymes:

| | |
|---|---|
| alpha-amylase | (*B. subtilis,* malt, *A. oryzae*) |
| Amino acid acylase | (Bacillus spp.) |
| Amyloglucosidase | (*A. niger,* Rhizopus sp.) |
| Bromelain | (Ananas) |
| Phisine | (Fig) |
| beta-galactosidase | (*A. niger*) |
| beta-glucanase | (*B. subtilis,* Aspergillus sp.) |
| Glucose-isomerase | (*L. brevis, P. notanum,* Strentomyces sy.) |
| Glucoseoxidase | (*A. niger*) |
| Hemicellulase | (*A. niger, Trichoderma reesei,* Bacillus spp.) |
| Invertase | (*S. cerevisae*) |
| Catalase | (*A. niger*) |
| Collagenase | (*Clostridium histolyticum*) |
| Xsylanase | (*A. niger, Trichoderma reesei,* Bacillus spp.) |
| Lactase | (*S. frigilis, S. lactis, E. coli,* Aspergillus sp.) |
| Lipase | (Mould, Yeast) |
| Naringinase | (*A. niger*) |
| Pancreatin | (Pancreas) |
| Papain | (Papaya) |
| Pectinase | (*A. niger,* Penicillium sp.) |
| Penicillinamidase | (Bacillus spp.) |
| Penicillinase | (Bacillus spp.) |
| Pepsin | (Animal abdomen) |
| Protease | (*A. oryzae, B. subtilis*) |
| Pullulanase | (*Aerobacter aerogenes*) |
| Isoamylase | (*Escherichia intermedia,* Pseudomonas sp.) |
| Rennin | (Calf stomach, *M. miehei, Endothia parasitica*) |
| Ribonuclease | (*B. subtilis,* Mould, *A. niger*) |
| Cellulase | (*A. niger, Trichoderma reesei*) |
| Streptokinase | (*Streptococcus hemolyticus*) |
| Trypsin | (Pancreas) |

EXAMPLE 1

Production of the β-lactamase Enzyme of *E. coli* from the *Bacillus subtilis* Strain The plasmid pKTH was opened by the Hind III enzyme, and to the cleavage site was joined a gene coding for β-lactamase of *E. coli* from which the promotor and excretion signal areas had been removed. The hybrid plasmid obtained was transformed into the competent *B. subtilis* IHO 6140 strain by selecting cells that had received the plasmid, on the basis of their kanamycin resistance, and the cells were cultivated on nutrient medium plates containing kanamycin. The transformants were screened with respect to the yield by suspending each colony in 100 μl 1 0.1 mM nitrosephin, 0.1M K-phosphate solution (pH 7.0). Liquid cultures were made of the colonies which gave a positive result in the nitrosephin test (the color of the solution changed into red) for determination of the activity of the β-lactamase enzyme produced. The IHO 6140 *B. subtilis* strain which had been transformed by the plasmid pKTH 50 was used as control. The strains were grown in a SMS solution (Spizizen minimal salts) to which had been added 0.5% glycerol, 1% soluble starch, and 5 μg/ml kanamycin. The cultures were grown at 37° C. while shaking. About 5 hours after a logarithmic growth period ($Klett_{67}{}^{\omega}250$), the cultures were centrifuged at 10,000 xg for 5 minutes and the supernatant was recovered. The cells were suspended in 0.1M potassium phosphate buffer (pH 2.0) to their original growing volume. The β-lactamase activity was determined in the cell and supernatant fractions by following spectrophotometrically the disintegration of cephalotin. The following results were obtained from the determination.

| | β-lactamase activity (U/ml)* | |
|---|---|---|
| | cells | supernatant |
| *B. subtilis* IHO 6140/pKTH 50 β-lactamase | 60 | 3000 |
| *B. subtilis* IHO 6140/pKTH 50 | <10 | <10 |

*) IU of β-lactamase disintegrates 1 μmol penicillin G in 1 minute at 37° C.

EXAMPLE 2

Production of Leukocyte Interferon in the *Bacillus subtilis* Strain

The plasmid pKTH 53 was cleaved by the Hind III enzyme, and to the cleavage site was joined the DNA sequence coding for the leukocyte interferon (α-2) from which the part coding for the excretion signal had been removed. The obtained hybrid plasmid was transformed into the competent IHO 6140 *B. subtilis* strain by selecting the cells that had obtained the plasmid, on the basis of their kanamycin resistance. The transformants were screened by a colony hybridization method (Grünstein, M. and Hogness, D. S., *Proc. Natl. Acad. Sci.* (*US*) 72:3961–3965 (1975)) while using as a probe the DNA coding for the interferon, marked $^{125}$J. The bacterium colonies containing interferon-DNA were grown in Luria broth to which had been added 2% soluble starch and 5 μg/ml kanamycin, while shaking at 37° C. The culture was centrifuged 4 hours after the logarithmic growth period ($Klett_{67}$ ∞300) at 10,000 xg for 5 min. The supernatant was recovered, and the cells were suspended to their original growing volume in a 0.9% NaCl solution. The interferon activity was determined in the cell and supernatant fractions. The *B. subtilis* IHO 6140/pKTH 53 strain was used as control in the determinations. The following results were obtained from the determinations.

| | Interferon activity (I.U./ml) | |
|---|---|---|
| | cells | supernatant |
| *B. subtilis* IHO 6140/pKTH 53-IF | 3000 | 200,000 |
| *B. subtilis* IHO 6140/pKTH 53 | <20 | <20 |

EXAMPLE 3

Expression Pertussis Toxin Subunits Inside *Bacillus subtilis*

From *Bordetella pertussis* strain Tohama a 4.5 kb EcoRI-BamHI chromosomal DNA restriction enzyme fragment, containing the pertussis toxin operon, was cloned, utilizing the previously published DNA sequence (Locht, C. et al., *Science* 232:1258–1264 (1986)). Using Amersham's in vitro oligo-directed mutagenesis system, a HindIII restriction enzyme site was created at the 5′ end of the DNA sequence coding for the mature part of pertussis toxin subunits $S_1$, $S_2$, $S_4$ and $S_5$, as described in co-pending U.S. application Ser. No. 129,387, now U.S. Pat. No. 5,010,015, filed on the same date as the present application, and incorporated herein by reference. The HindIII site in the gene coding for $S_3$ was created with an oligolinker ligated into the FokI site positioned immediately downstream of the 5′ end of the DNA sequence coding for the mature part of $S_3$.

To express the pertussis toxin subunits, HindIII fragments containing the coding regions for the subunits were ligated with HindIII cut expression vectors. In this way, the transcription of the subunit's genes could be controlled by the amylase promoter (Palva, I., et al., *Gene* 15:43–51 (1981)) in the vector. The procedure for expressing $S_4$ was different. The HindIII fragments coding for $S_4$ were subjected to a fill-in reaction with Klenow fragment, and the expression vector, to be ligated with the $S_4$ coding fragment, was digested with EcoRI, followed by a partial $S_1$ exonuclease digestion and a fill-in reaction with Klenow fragment. *Bacillus subtilis* strain BRB41 (Palva, I., et al., *Gene* 22:229–235 (1983)) was transformed with the ligation mixes. The ability of the clones to express the pertussis toxin subunits was analyzed by SDS-polyacrylamide gel electrophoresis, followed by Western blotting. A rabbit antiserum recognizing all subunits and the Protoblot immunoscreening system was used to visualize the immunoreactive proteins. All subunits could be expressed inside *Bacillus subtilis.*

EXAMPLE 4

Expression of Chloramphenicol Acetyl Transferase (cat) Gene in *B. subtilis*

The chloramphenicol acetyl transferase (cat) gene from *B. pumilus* is available as a promoterless derivative in the plasmid pPL603 (Williams et al., *J. Bacteriol.* 146:1162–1165 (1981)). The AhaIII restriction endonuclease cleaves pPL603 precisely at the 5′ end of the cat gene, resulting in a 700 bp AhaIII-XbaI fragment containing the structural cat gene.

To clone this gene in *B. subtilis,* the plasmid pKTH 39 was linearized with EcoRI, treated with S1 nuclease and Klenow polymerase to generate blunt ends, and subsequently ligated to the corresponding 700 bp AhaIII-XbaI fragment containing the cat gene.

The resulting ligation mixture was transformed into competent *B. subtilis* BRB 41 cells. Chloramphenicol-resistant ($Cm^r$, 5 μg/ml) colonies were selected, and plasmid DNA from two independent $Cm^r$ colonies was analyzed to confirm the correct DNA structure. The results of CAT assay performed from liquid cultures (as described in Shaw, *Meth. Enzymol.* 43:737–755 (1975)) were as follows:

| Turbidity | BRB41 (PKTH 39-cat) | | BRB41 | |
|---|---|---|---|---|
| ($Klett_{67}$) | cells | sup | cells | sup |
| 160 | 0.92 | nr⁻ | nr | nr |
| 250 ($Klett_{100}$ + 5 h) | 4.7 | nr | nr | nr |

⁻nr, no results: below detection limit of assay.

The structure of the plasmid pKTH 39 containing the cat gene at the region of the ligation of the cat gene to the deleted non-functional α-amylase signal sequence was as follows:

. . . ATG ATT CAA AAA CGA AAG CGG AAT TTA AGC TT . . .

truncated a-amylase signal sequence — cat structural gene

EXAMPLE 5

Production of Pertussis Toxin S4 Subunit in *B. subtilis*

Expression of the pertussis toxin S4 subunit in *B. subtilis* is described in Example 4 of co-pending U.S. application Ser. No. 129,387, now U.S. Pat. No. 5,010,015, supra, using the pKTH 39-based expression plasmid pKTH 229. According to this construction, a hybrid S4 subunit is generated containing additional amino acid residues from the a-amylase vector, and lacking several N-terminus amino acids of the S4 subunit.

The S4 subunit was expressed according to the present invention as follows. A plasmid construction was designed to leave only the initiation methionine at the N-terminus of the intact S4 polypeptide. The necessary modifications to the DNA were made employing the well-known polymerase chain reaction (PCR) method, using the plasmid pKTH 229 as a template. The PCR fragment had the following nucleotide sequence at the joint region:

```
...   f.met asp  val  pro  tyr  val     ...
...   ATG   GAC  GTT  CCT  TAT  GTG      ...
truncated a-amylase      intact S4 subunit sequence
signal sequence
```

The resulting PCR fragment was ligated to the plasmid pUB110 and transformed into *B. subtilis* BRB41 cells. Western blotting revealed colonies producing the S4 subunit intracellularly.

What is claimed is:

1. A recombinant DNA molecule comprising (1) the regulation sequence of the α-amylase gene of *Bacillus amyloliquefaciens,* (2) DNA encoding a truncated, non-functional signal sequence of the α-amylase gene of *Bacillus amyloliquefaciens* wherein said DNA comprises DNA encoding at least the N-terminal initiation methionine (Met) and the next six adjacent N-terminal amino acids of the wild type of said signal sequence, but not DNA encoding the seven C-terminal amino acids of the wild type of said signal sequence, and (3) DNA encoding amino acids of a desired protein or polypeptide wherein said DNA encoding said desired protein or polypeptide Is downstream from and in phase with said regulation sequence and said DNA encoding said non-functional signal sequence.

2. A recombinant DNA molecule of claim 1 wherein said truncated, non-functional signal sequence is from a plasmid selected from the group consisting of pKTH 39, pKTH 1781 and pKTH 1784 as shown in FIG. 5.

3. A recombinant DNA molecule of claim 1, wherein said truncated, non-functional signal sequence comprises amino acids encoded by ATG ATT CAA AAA CGA AAG CGG.

4. A recombinant DNA molecule of claim 1, wherein said truncated, non-functional signal sequence comprises amino acids encoded by ATG ATT CAA AAA CGA AAG CGG AAT TCC.

5. A recombinant DNA molecule of claim 1, wherein said truncated, non-functional signal sequence comprises amino acids encoded by ATG ATT CAA AAA CGA AAG CGG AAT TCG GAA GCT TXX.

6. A recombinant DNA molecule of claim 1, wherein said truncated, non-functional signal sequence comprises amino acids encoded by ATG ATT CAA AAA CGA AAG CGG AAT TTA AGC TTX.

7. A recombinant DNA molecule of claim 1 wherein said DNA encoding amino acids of a desired protein or polypeptide is selected from the group consisting of DNA encoding chloramphenicol acetyl transferase and DNA encoding pertussis toxin or subunits thereof.

8. A vector comprising a recombinant DNA molecule of claim 1.

9. The vector of claim 8, wherein said DNA encoding amino acids of a desired protein or polypeptide is selected from the group consisting of DNA encoding chloramphenicol acetyl transferase and DNA encoding pertussis toxin or subunits thereof.

10. A Bacillus host comprising the vector of claim 8.

11. A Bacillus host comprising the vector of claim 9.

12. A method for obtaining intracellular expression of a desired homologous or heterologous protein, or polypeptide, in a Bacillus host, comprising (a) transforming a desired Bacillus host with a recombinant DNA molecule comprising (1) the regulation sequence of the α-amylase gene of *Bacillus amyloliquefaciens,* (2) DNA encoding a truncated, non-functional signal sequence of the α-amylase gene of *Bacillus amyloliquefaciens* wherein said DNA comprises DNA encoding at least the N-terminal initiation methionine (Met) and the next six adjacent N-terminal amino acids of the wild type of said signal sequence, but not DNA encoding the seven C-terminal amino acids of the wild type of said signal sequence and (3) DNA encoding amino acids of a desired protein or polypeptide wherein said DNA encoding said desired protein or polypeptide is downstream from and in phase with said regulation sequence and said DNA encoding said non-functional signal sequence, and (b) culturing the Bacillus host of step (a) under conditions allowing Intracellular expression of said desired homologous or heterologous protein or polypeptide.

* * * * *

UNITED STATES PATENT AND TRADEMARK OFFICE
CERTIFICATE OF CORRECTION

PATENT NO. : 5,380,653
DATED : January 10, 1995
INVENTOR(S) : Ilkka Palva

It is certified that error appears in the above-identified patent and that said Letters Patent is hereby corrected as shown below:

Cover page, title "EXPRESSION VECTORS AND METHODS FOR INTRACELLULAR PROTEIN PRODUCTION IN BASCILLUS" should read -- EXPRESSION VECTORS AND METHODS FOR INTRACELLULAR PROTEIN PRODUCTION IN BACILLUS --.

Cover page, References Cited, Foreign Patent Documents:
"0281530 7/1988 European Pat. Off." should read -- 0281530 9/1988 European Pat. Off. --.
"2091268 12/1981 Great Britain should read -- 2091268 7/1982 United Kingdom. --.

Column 1, line 4, "BASCILLUS" should read -- BACILLUS --.

Column 7, line 14, "$\geqq 15 \times 10^6$" should read -- $\geq 15 \times 10^6$ --.

Column 17, line 59, "129,387" should read -- 129,357 --.

Column 18, line 50, "PKTH" should read -- pKTH --.

Column 18, line 52, "nr-" should read -- $nr^-$ --.

Column 18, line 55, "-nr" should read -- $^-nr$ --.

Column 19, line 6, "129,387" should read -- 129,357 --.

Column 19, line 45, "Is" should read -- is --.

Column 20, line 1, "ATG ATT CAA AAA CGA AAG CGG." should read -- ATG ATT CAA AAA CGA AAG CGG AAT TCC. --.

Column 20, line 5, "ATG ATT CAA AAA CGA AAG CGG AAT TCC." should read -- ATG ATT CAA AAA CGA AAG CGG AAT TCG GAA GCT TXX. --.

Column 20, line 9, "ATG ATT CAA AAA CGA AAG CGG AAT TCG GAA GCT TXX." should read -- ATG ATT CAA AAA CGA AAG CGG AAT TTA AGC TTX. --.

UNITED STATES PATENT AND TRADEMARK OFFICE
CERTIFICATE OF CORRECTION

PATENT NO. :
DATED : 5,380,653
INVENTOR(S) : January 10, 1995
Ilkka Palva

It is certified that error appears in the above-identified patent and that said Letters Patent is hereby corrected as shown below:

Column 20, line 11, delete Paragraph "6. A recombinant DNA molecule ... TTA AGC TTX."

Column 20, line 15, "7." should read -- 6. --.

Column 20, line 20, "8." should read -- 7. --.

Column 20, line 22, "9. The vector of claim 8" should read -- 8. The vector of claim 7 --.

Column 20, line 27, "10. A Bacillus host comprising the vector of claim 8." should read -- 9. A Bacillus host comprising the vector of claim 7. --.

Column 20, line 28, "11. A Bacillus host comprising the vector of claim 9." should read -- 10. A Bacillus host comprising the vector of claim 8. --.

Column 20, line 29, "12." should read -- 11. --.

Column 20, line 50, "Intracellular" should read -- intracellular --.

Column 20, line 53 should read -- 12. A recombinant DNA molecule of claim 1, wherein said truncated, non-functional signal sequence comprises amino acids encoded by ATG ATT CAA AAA CGA AAG CGG. --.

Signed and Sealed this

First Day of August, 1995

Attest:

Bruce Lehman

BRUCE LEHMAN

*Attesting Officer* *Commissioner of Patents and Trademarks*